United States Patent
Farooqui

(10) Patent No.: US 10,070,808 B2
(45) Date of Patent: Sep. 11, 2018

(54) APPARATUS FOR IN VIVO DETECTION AND QUANTIFICATION OF ANALYTES IN THE PERITONEAL FLUID

(71) Applicants: National Guard Health Affairs, Riyadh (SA); King Saud Bin Abdulaziz University for Health Sciences, Riyadh (SA); King Abdullah International Medical Research Center, Riyadh (SA)

(72) Inventor: Mahfooz Alam Farooqui, Riyadh (SA)

(73) Assignees: National Guard Health Affairs, Riyadh (SA); King Saud Bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 161 days.

(21) Appl. No.: 15/173,016

(22) Filed: Jun. 3, 2016

(65) Prior Publication Data

US 2017/0347926 A1    Dec. 7, 2017

(51) Int. Cl.
*A61B 5/05*        (2006.01)
*A61B 5/145*      (2006.01)
*A61B 5/00*        (2006.01)

(52) U.S. Cl.
CPC ........ *A61B 5/14503* (2013.01); *A61B 5/0017* (2013.01); *A61B 5/0022* (2013.01);
(Continued)

(58) Field of Classification Search
CPC ....... A61B 5/145; A61B 5/00; A61B 5/14503; A61B 5/14532; A61B 5/14546;
(Continued)

(56) References Cited

U.S. PATENT DOCUMENTS

| | | | |
|---|---|---|---|
| 3,911,901 A | 10/1975 | Niedrach et al. | |
| 4,950,259 A | 8/1990 | Geary et al. | |

(Continued)

FOREIGN PATENT DOCUMENTS

| | | |
|---|---|---|
| EP | 1638483 A1 | 3/2006 |
| WO | WO 2009/094035 A1 | 7/2009 |
| WO | WO 2015/021063 A1 | 2/2015 |

OTHER PUBLICATIONS

Rolfe P, "In vivo chemical sensors for intensive-care monitoring", PubMed/http://www.ncbi.nlm.nih.gov/pubmed/2198408, vol. B34-47, May 28, 1990, pp. 1.

(Continued)

*Primary Examiner* — Jacqueline Cheng
*Assistant Examiner* — Eric Messersmith
(74) *Attorney, Agent, or Firm* — Oblon, McClelland, Maier & Neustadt, L.L.P.

(57) ABSTRACT

A device for in vivo detecting and quantifying a concentration of an analyte in a peritoneal fluid of a subject. The device includes (a) a catheter having an open proximal end configured to be disposed external to the subject, an open distal end configured to be disposed within the peritoneal cavity comprising the peritoneal fluid, an anchor portion, an outer wall, and an inner wall, (b) a sensor disposed adjacent to the open distal end and configured to detect and quantify the concentration of the analyte in the peritoneal fluid, and (c) a main control unit disposed external to the subject, connected to the sensor via a wire, and configured to control the sensor, receive and store detection and quantification data from the sensor, and transmit the data to a second device. A portion of the wire is disposed between the inner wall and the outer wall of the catheter.

17 Claims, 5 Drawing Sheets

(52) U.S. Cl.
CPC ........ *A61B 5/0024* (2013.01); *A61B 5/14507* (2013.01); *A61B 5/14532* (2013.01); *A61B 5/14546* (2013.01); *A61B 5/6853* (2013.01); *A61B 5/7282* (2013.01); *A61B 5/742* (2013.01); *A61B 5/746* (2013.01); *A61B 2562/222* (2013.01)

(58) Field of Classification Search
CPC ..... A61B 5/742; A61B 5/0017; A61B 5/0024; A61B 5/6853; A61B 5/14507; A61B 5/7282; A61B 5/746; A61B 5/0022; A61B 2562/222
See application file for complete search history.

(56) References Cited

U.S. PATENT DOCUMENTS

| | | | |
|---|---|---|---|
| 5,520,178 A | 5/1996 | Dahn et al. | |
| 6,694,161 B2 | 2/2004 | Mehrotra | |
| 8,926,585 B2 | 1/2015 | Brauker et al. | |
| 9,078,972 B2 | 7/2015 | Gupta et al. | |
| 2004/0180391 A1 | 9/2004 | Gratzl et al. | |
| 2010/0261987 A1* | 10/2010 | Kamath | A61B 5/14532 600/365 |
| 2011/0201911 A1* | 8/2011 | Johnson | A61B 5/14532 600/365 |
| 2017/0020422 A1* | 1/2017 | Bigelow | A61B 5/6848 |
| 2017/0072125 A1* | 3/2017 | Wallen S | A61M 1/285 |
| 2017/0281062 A1* | 10/2017 | Burnett | A61B 5/14532 |

OTHER PUBLICATIONS

C. Eddy, et. al, "Near-Infrared Spectroscopy for Measuring Urea in Hemodialysis Fluids", Clinical Chemistry, 2001, pp. 1279-1286.

N.S. Oliver, et al., "Glucose sensors: a review of current and emerging technology" 2009, Diabetic Medicine, vol. 26 pp. 197-210.

* cited by examiner

APPARATUS FOR IN VIVO DETECTION AND QUANTIFICATION OF ANALYTES IN THE PERITONEAL FLUID

BACKGROUND OF THE INVENTION

Technical Field

The present disclosure relates to devices for in vivo detecting and quantifying concentration of an analyte in the peritoneal fluid of a subject, such as a human or an animal. More specifically, the present disclosure relates to a device comprising a catheter configured for insertion through the abdominal wall into the peritoneal cavity containing the peritoneal fluid of the subject, a sensor attached to the catheter, and a main control unit connected to the sensor and configured to control the sensor and to receive, store, and transmit the detection and quantification data obtained by the sensor.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, is neither expressly nor impliedly admitted as prior art against the present invention.

In medicine, a catheter is a thin tube made from medical grade materials serving a broad range of functions. Catheters are medical devices that can be inserted in the body to treat diseases or perform a surgical procedure. By modifying the material or adjusting the way catheters are manufactured, it is possible to tailor catheters for cardiovascular, urological, gastrointestinal, neurovascular, and ophthalmic applications.

Catheters can be inserted into a bodily organ, cavity, duct, or vessel. Functionally, they allow drainage, administration of fluids or gases, access by surgical instruments, and also perform a wide variety of other tasks depending on the type of catheter. For example, a uretic catheter allows draining urine from the urinary bladder. Other types of catheters perform draining of urine from the kidney, draining of fluids from an abnormal abscess, and intravenous administration of fluids, etc.

In peritoneal dialysis for a patient with severe chronic kidney disease, a peritoneal dialysis catheter is placed surgically in the peritoneal cavity of the patient's abdomen. A sterile peritoneal dialysis solution called dialysate is introduced into the peritoneal cavity through the catheter. With the peritoneal membrane as a natural filter, the peritoneal dialysis solution removes the patient body's wastes, extra salt and water. After the filtering process is finished, the spent peritoneal dialysis solution is drained from the peritoneal cavity through the catheter.

It is an object of this disclosure to provide a device for in vivo detecting and quantifying concentration of an analyte in the peritoneal fluid in the peritoneal cavity of a subject, preferably in a peritoneal dialysis setting. The device comprises a catheter, preferably a peritoneal dialysis catheter configured for insertion through the abdominal wall into the peritoneal cavity containing the peritoneal fluid of the subject and suited for introduction of a fresh peritoneal dialysis solution into the peritoneal cavity and draining of a spent peritoneal dialysis solution from the peritoneal cavity, at least one sensor attached to the catheter, and a main control unit connected to the sensors via at least one wire. The sensors are configured to contact the peritoneal fluid and to detect and quantify the concentrations of analytes in the peritoneal fluid (e.g. bodily fluids in the peritoneal cavity, a peritoneal dialysis solution, or a mix of bodily fluids and a peritoneal dialysis solution) the sensors are exposed to, preferably in real time, more preferably also continuously. The main control unit is configured to control the sensors, to receive and store the detection and quantification data from the sensors, and to transmit the data to a second device, for example, a computer, a smart phone, and a smart watch. The disclosed device may be advantageously used in a peritoneal dialysis procedure to help monitor the progress and status of the procedure, take timely actions based on the real time data, and make informed medical decisions by the patient and a health care provider.

BRIEF SUMMARY OF THE INVENTION

The present disclosure relates to a device for in vivo detecting and quantifying a concentration of at least one analyte in a peritoneal fluid of a subject. The device includes (a) a catheter configured for insertion through an abdominal wall into a peritoneal cavity comprising the peritoneal fluid of the subject, wherein the catheter comprises an elongated tube having an open proximal end, an open distal end, an anchor portion disposed between the open proximal end and the open distal end, an outer wall, and an inner wall disposed within the outer wall and defining a central lumen for conveying the peritoneal fluid, wherein the open proximal end is configured to be disposed external to the subject, the open distal end is configured to be disposed within the peritoneal cavity of the subject, and the anchor portion is configured to be disposed within and anchored to the abdominal wall, (b) at least one sensor disposed on a surface of the inner wall of the catheter at or adjacent to the open distal end, wherein the at least one sensor is configured to contact the peritoneal fluid and to detect and quantify the concentration of at least one analyte in the peritoneal fluid in real time, wherein the at least one analyte is selected from the group consisting of glucose, hydrogen ion, urea, and creatinine, and (c) a main control unit disposed external to the subject and connected to the at least one sensor via at least one wire, wherein at least a portion of the at least one wire is disposed between the inner wall and the outer wall of the catheter, wherein the main control unit is configured to control the at least one sensor, to receive and store data of the detection and quantification of the at least one analyte in the peritoneal fluid from the at least one sensor via the at least one wire, and to transmit the data to a second device.

In one or more embodiments, the catheter further comprises a plurality of openings disposed on a distal portion of the catheter, wherein the plurality of openings pass through the outer wall and the inner wall without the at least one wire therebetween, and wherein the distal portion of the catheter is configured to contact the peritoneal fluid.

In one or more embodiments, the main control unit comprises a display for displaying the data.

In one or more embodiments, the main control unit is further configured to analyze the data.

In one or more embodiments, the main control unit is configured to transmit the data to the second device via a wired link, a wireless link, or a combination thereof.

In one or more embodiments, the wireless link is at least one selected from the group consisting of a Bluetooth link, an infrared link, a Wi-Fi link, and a satellite link.

In one or more embodiments, the second device is at least one selected from the group consisting of a computer, a smart phone, a smart watch, a pager, and a cloud computer server.

In one or more embodiments, the second device is configured to analyze the data.

In one or more embodiments, the subject is a human or an animal.

In one or more embodiments, the at least one wire is made of a non-magnetic conductive material.

In one or more embodiments, the non-magnetic conductive material is at least one selected from the group consisting of aluminum, copper, zinc, titanium, gold, silver, platinum, graphite, a polyfluorene, a polyphenylene, a polypyrene, a polyazulene, a polynaphthalene, a polypyrrole, a polycarbazole, a polyindole, a polyazepine, a polyaniline, a polythiophene, poly(3,4-ethylenedioxythiophene), poly(p-phenylene sulfide), a polyacetylene, and polyphenylene vinylene.

In one or more embodiments, a Dacron cuff is disposed on the outer wall of the anchor portion for anchoring the catheter in the abdominal wall.

In one or more embodiments, the device further comprises an extension set connected to the open proximal end of the catheter.

In one or more embodiments, the main control unit and/or the second device are configured to generate and/or transmit an alert if the data vary from a baseline.

In one or more embodiments, the baseline is a baseline previously established from the subject.

In one or more embodiments, the main control unit and/or the second device are configured to determine a relationship of the concentration of the at least one analyte of glucose, hydrogen ion, urea, and creatinine with time based on the data received from the at least one sensor, wherein the relationship is represented by a curve indicative of the concentration at each time, and wherein the main control unit and/or the second device are configured to calculate an area under the curve indicative of the concentration at each time.

In one or more embodiments, the main control unit and/or the second device are further configured to generate and/or transmit an alert if the area under the curve varies from a pre-set value.

In one or more embodiments, the main control unit and/or the second device are configured to determine a relationship of the concentration of the at least one analyte of glucose, hydrogen ion, urea, and creatinine with time based on the data received from the at least one sensor and calculate a rate of change in the concentration of the at least one analyte of glucose, hydrogen ion, urea, and creatinine at each time and/or over a period of time based on the relationship.

In one or more embodiments, the main control unit and/or the second device are further configured to generate and/or transmit an alert if the rate of change varies from a pre-set value.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
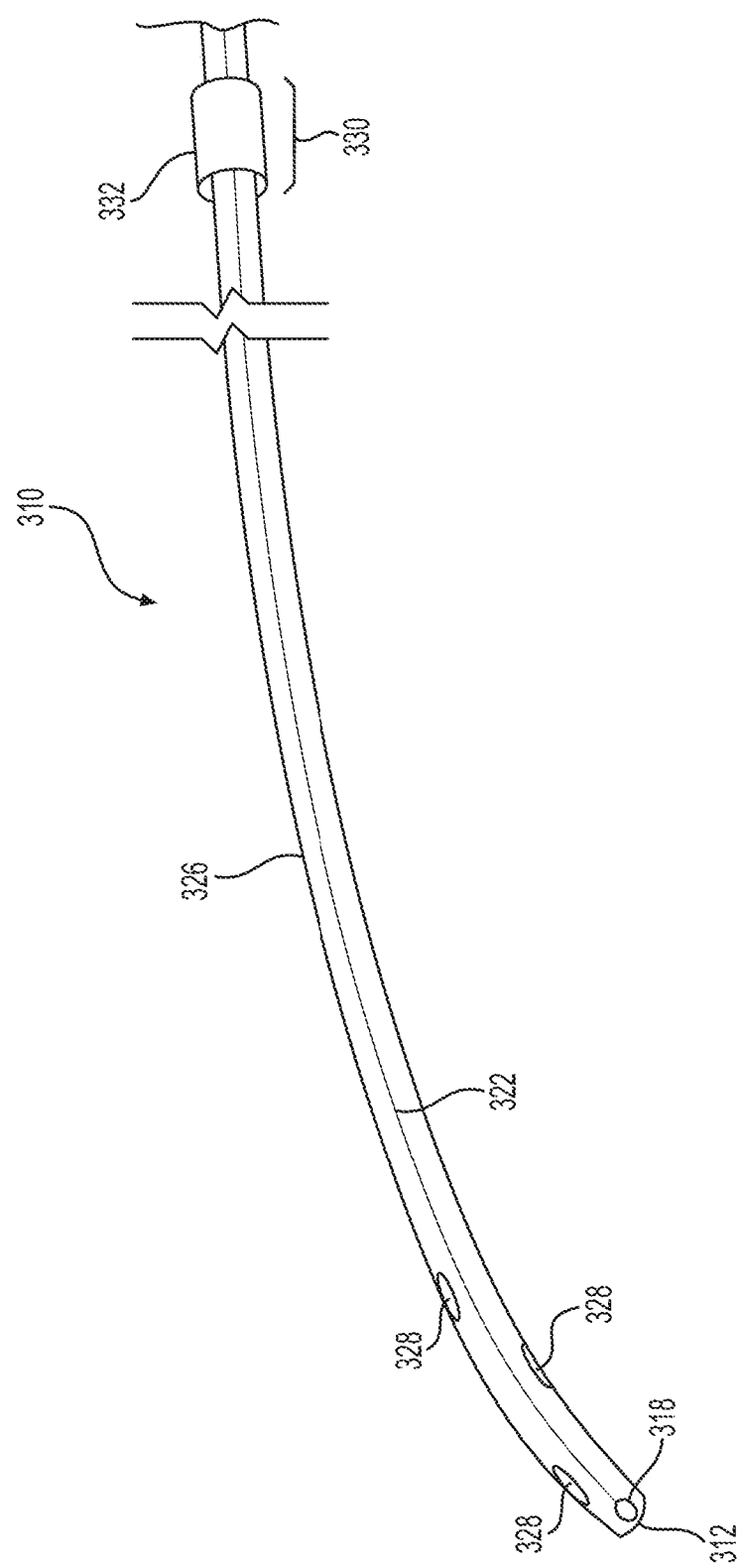
FIG. 1 is an embodiment of the device, particularly showing a distal portion ending at the open distal end 312 and the anchor portion 330 of the catheter 310.
Figure 2:
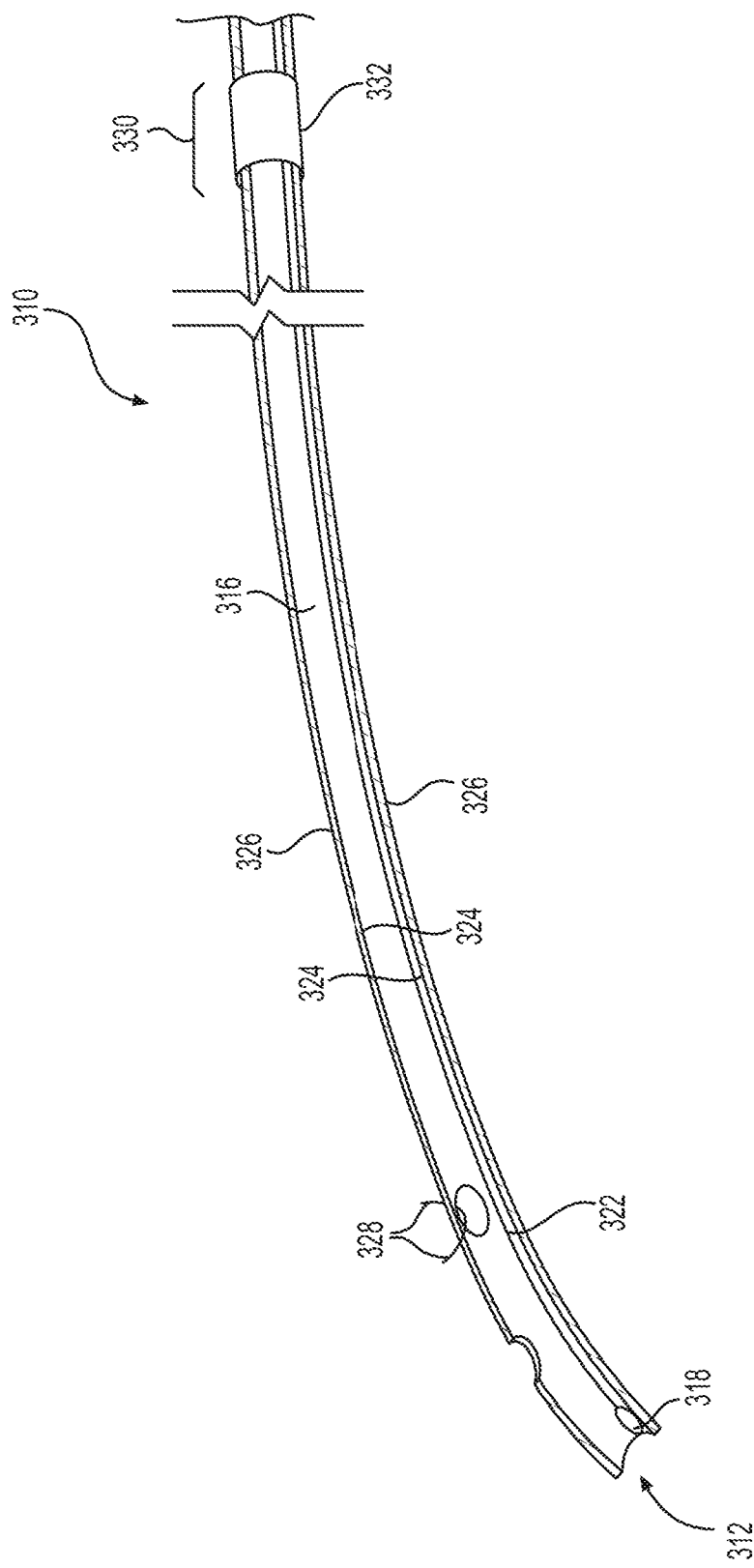
FIG. 2 provides a longitudinal cross-sectional view of the catheter 310 of the device shown in FIG. 1.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Embodiments of the device for in vivo detecting and quantifying a concentration of at least one analyte in a peritoneal fluid of a subject are shown in FIGS. 1-4. The device includes (a) a catheter 310 configured for insertion through an abdominal wall 600 into a peritoneal cavity 606 comprising the peritoneal fluid of the subject, wherein the catheter 310 comprises an elongated tube having an open proximal end 314, an open distal end 312, an anchor portion 330 disposed between the open proximal end 314 and the open distal end 312, an outer wall 326, and an inner wall 324 disposed within the outer wall 326 and defining a central lumen 316 for conveying the peritoneal fluid, wherein the open proximal end 314 is configured to be disposed external to the subject, the open distal end 312 is configured to be disposed within the peritoneal cavity 606 of the subject, and the anchor portion 330 is configured to be disposed within and anchored to the abdominal wall 600, (b) at least one sensor 318 disposed on a surface of the inner wall 324 of the catheter 310 at or adjacent to the open distal end 312 and configured to contact the peritoneal fluid and to detect and quantify the concentration of at least one analyte selected from the group consisting of glucose, hydrogen ion, urea, and creatinine in the peritoneal fluid, preferably in real time, and (c) a main control unit 320 disposed external to the subject and connected to the at least one sensor 318 via at least one wire 322, wherein at least a portion of the at least one wire 322 is disposed between the inner wall 324 and the outer wall 326 of the catheter 310, wherein the main control unit 320 is configured to control the at least one sensor 318, to receive and store data of the detection and quantification of the at least one analyte in the peritoneal fluid from the at least one sensor 318 via the at least one wire 322, and to transmit the data to a second device.

The device may be advantageously used for peritoneal dialysis. Peritoneal dialysis (PD) is a treatment for patients with severe chronic kidney disease, since peritoneal dialysis replaces the work of the kidney. This type of dialysis uses the patient's peritoneum in the abdomen as a membrane across which fluids and dissolved substances (electrolytes, urea, glucose, albumin, osmotically active particles, and other small molecules) are exchanged from the blood. A fresh peritoneal dialysis solution may be introduced through the catheter of the device into the peritoneal cavity of the abdomen and a spent peritoneal dialysis solution may be flushed out through the catheter of the device either every night while the patient sleeps (automatic peritoneal dialysis) or via regular exchanges throughout the day (continuous ambulatory peritoneal dialysis).

There are three main steps in a typical peritoneal dialysis procedure: 1. Fill: A fresh peritoneal dialysis solution enters the peritoneal cavity of the patient; 2. Dwell: While the peritoneal dialysis solution is in the peritoneal cavity, extra fluid and waste travel across the peritoneal membrane into the peritoneal dialysis solution; and 3. Drain: After a few hours, the spent peritoneal dialysis solution is drained and replaced with a new (fresh) peritoneal dialysis solution. More specifically, the abdomen is cleaned in preparation for surgery, and the catheter is surgically inserted with one (distal) end in the peritoneal cavity of the abdomen and the other (proximal end) protruding from the skin. Before each infusion, the catheter is cleaned, and flow into and out the peritoneal cavity of the abdomen is tested. In a typical adult human subject, two to three liters of a fresh peritoneal dialysis solution may be introduced to the peritoneal cavity of the abdomen over the next ten to fifteen minutes. The peritoneal dialysis solution, referred to as dialysate, remains in the peritoneal cavity of the abdomen and waste products diffuse across the peritoneum from the underlying blood vessels. After a variable period of time depending on the treatment (usually 4-6 hours), the spent peritoneal dialysis solution is removed and replaced with a fresh peritoneal dialysis solution. This can occur automatically while the patient is sleeping (automated peritoneal dialysis, APD), or during the day by keeping two liters of peritoneal dialysis solution in the peritoneal cavity of the abdomen at all times, exchanging the peritoneal dialysis solution four to six times per day (continuous ambulatory peritoneal dialysis, CAPD).

The peritoneal dialysis solution used typically contains sodium, chloride, lactate or bicarbonate and a high percentage of glucose (e.g. 1-5% w/v) to ensure hyperosmolarity. The amount of dialysis that occurs depends on the volume of the peritoneal dialysis solution, the regularity of the exchange (each cycle of draining of a spent peritoneal dialysis solution and refilling of a fresh peritoneal dialysis solution is called an exchange) and the glucose concentration of the peritoneal dialysis solution. APD cycles between 3 and 10 dwells per night, while CAPD involves four dwells per day of 2-3 liters per dwell, with the peritoneal dialysis solution remaining in the peritoneal cavity of the abdomen for 4-8 hours at each dwell. The viscera accounts for roughly four-fifths of the total surface area of the membrane, but the parietal peritoneum is the more important of the two portions for peritoneal dialysis. Two complementary models explain dialysis across the membrane—the three pore model (in which molecules are exchanged across membranes which sieve molecules, either proteins, electrolytes or water, based on the size of the pores) and the distributed model (which emphasizes the role of capillaries and the solution's ability to increase the number of active capillaries involved in peritoneal dialysis). The high concentration of glucose drives the filtration of fluid by osmosis (osmotic ultrafiltration) from the peritoneal capillaries to the peritoneal cavity. Glucose diffuses rather rapidly from the dialysate to the blood (capillaries). After 4-6 h of the dwell the glucose osmotic gradient usually becomes too low to allow for further osmotic ultrafiltration. Therefore, the dialysate will now be reabsorbed from the peritoneal cavity to the capillaries by means of the plasma colloid osmotic pressure, which exceeds the colloid osmotic pressure in the peritoneum by approximately 18-20 mmHg (cf. the Starling mechanism). Lymphatic absorption will also to some extent contribute to the reabsorption of fluid from the peritoneal cavity to the plasma. Patients with a high water permeability (ultrafiltration-coefficient) of the peritoneal membrane can have an increased reabsorption rate of fluid from the peritoneum by the end of the dwell. The ability to exchange small solutes and fluid in-between the peritoneum and the plasma can be classified as high (fast), low (slow) or intermediate. High transporters tend to diffuse substances well (easily exchanging small molecules between blood and the peritoneal dialysis solution, with somewhat improved results with frequent, short-duration dwells such as with APD), while low transporters have a higher ultrafiltration (due to the slower reabsorption of glucose from the peritoneal cavity), though in practice either type of transporter can generally be managed through the appropriate use of either APD or CAPD.

In one embodiment, the subject is a human. In another embodiment, the subject is an animal, such as a mouse, a dog, a cat, etc. When the subject is an animal, a peritoneal dialysis procedure similar to that for a human patient described above may be performed by modifying, for example, the volume of the peritoneal dialysis solution used for each dwell based on the size of the peritoneal cavity of the animal, the dwell time, and the length and diameter of the catheter 310 described below.

In a preferred embodiment, the catheter of the device has the characteristics suitable for peritoneal dialysis. For example, the catheter 310 comprises an elongated tube configured for insertion through the abdominal wall 600 into the peritoneal cavity 606 of the subject and made from an inert pliable medical grade Silastic (trademark) silicone rubber supplied by Dow Corning or similar flexible soft plastic equivalent to permit a distal portion of the catheter to lie loosely and freely in the peritoneal cavity.

By appropriately adjusting the length and diameter of the catheter 310 based on the type (e.g. a human or an animal) and size (e.g. an adult or a child) of the subject, the open distal end 312 may be configured to extend into the peritoneal cavity 606 of the subject to allow the sensors 318 to contact the peritoneal fluid and detect and quantify the concentrations of analytes in the peritoneal fluid.

As mentioned above, a typical peritoneal dialysis solution (dialysate) contains a high concentration of glucose to effect hyperosmolarity that drives the filtration of fluid by osmosis from the blood to the peritoneal cavity. During a peritoneal dialysis treatment, i.e. the dwell time, the peritoneal cavity of the subject is filled with a mix of bodily fluids containing, e.g. creatinine and urea, and the peritoneal dialysis solution. Before and after a peritoneal dialysis treatment, substantially only bodily fluids are present in the peritoneal cavity of the subject. Herein the term "peritoneal fluid" refers to any combination of fluids (e.g. bodily fluids, peritoneal dialysis solution, or a mix thereof), unless otherwise evident from the context.

Likewise, by appropriately adjusting the length of the catheter 310, the open proximal end 314 is preferably disposed external to the subject for conveniently administering and/or disposing of the peritoneal fluid. The catheter 310 has a central lumen 316 defined by the inner wall 324 of the catheter 310. The central lumen 316 is configured to convey a peritoneal dialysis solution to the peritoneal cavity in a proximal end-to-distal end flow direction and/or to convey a spent peritoneal dialysis solution from the peritoneal cavity in a distal end-to proximal end flow direction.

Since the device is contemplated to be able to detect and quantify analytes in the peritoneal fluid in a peritoneal dialysis procedure, particularly during the "dwell" step when the peritoneal solution is in the peritoneal cavity 606 of the subject to remove waste products from the blood, the sensors 318 of the device are preferably disposed at or adjacent to the open distal end 312 on a surface of the inner wall 324 of the catheter 310 to achieve a maximal exposure of the sensors 318 to the peritoneal fluid in the peritoneal cavity 606. In some embodiments, additional sensors may be disposed at other locations within the inner wall of the catheter 310 if additional determinations of the concentrations of the analytes are needed as the peritoneal fluid fills in or travels through the central lumen 316 of the catheter 310.

In another embodiment, the sensors 318 may be disposed on a surface of the inner wall 324 at any segment of the catheter 310 between the open distal end 312 and the open proximal end 314. The location of the sensors depends on, for example, where the sensors have an efficient contact with or exposure to the analytes in the peritoneal fluid, where the concentrations of the analytes contacting the sensors are representative of the peritoneal fluid and/or above the detection limits of the sensors, and how often the analytes are desired to be detected and quantified inside the central lumen 316 of the catheter 310.

To increase the amount of the peritoneal fluid drawn from the peritoneal cavity into the central lumen 316 of the catheter 310, in a preferred embodiment, the catheter 310 may further comprise a plurality of openings or holes 328 on a distal portion of the catheter 310 configured to extend to the peritoneal cavity and contact the peritoneal fluid in the peritoneal cavity. The openings 328 pass through both the outer wall 326 and the inner wall 324 to allow entry of the peritoneal fluid into the central lumen 316 of the catheter 310 from the peritoneal cavity. However, the openings 328 cannot be on a wall area of the catheter 310 where a portion of the wire 322 lies between the outer wall 326 and the inner wall 324 of the catheter 310 to maintain the integrity of the wire 322.

Between the open proximal end 314 and the open distal end 312, there is the anchor portion 330 to be disposed within the abdominal wall 600. In one embodiment, the anchor portion 330 of the catheter 310 may be anchored to the abdominal wall 600 by tying the anchor portion 330 to the abdominal wall 600, e.g. with a piece of suture, or preferably, by disposing a Dacron (trademark) cuff 332 on the outer wall of the anchor portion 330 by, for example, gluing, sewing, or frictional fitting the Dacron cuff in place. Dacron is a trademark or brand name for polyethylene terephthalate (PET or PETE), the most common thermoplastic polymer resin of the polyester family used in fibers for clothing, containers for liquids and foods, thermoforming for manufacturing, and in combination with glass fiber for engineering resins. The Dacron cuff 332 may be a sheath of dense, flexible, tightly woven felt synthetic fabric which surrounds the outer wall of the anchor portion 330 of the catheter 310 to prevent accidental displacement of the catheter 310. The Dacron cuff 332 also serves as a biological barrier against bacterial invasion at the interface between the implanted foreign synthetic materials, e.g. silicone rubber, of the catheter 310 and the abdominal wall skin. After implantation of the catheter 310, body tissues grow into the Dacron cuff, thus stabilizing the catheter 310 and forming a biological barrier against infection. The growth of fibroblasts and tissues into the meshwork of the Dacron cuff 332 not only fixes the catheter 310 in place and prevents sliding, but also provides an efficient barrier against bacterial invasion. The dimension of the Dacron cuff 332 may vary, depending on the type and size of the subject, the diameter of the catheter, and the area of the interface between the catheter and the abdominal wall skin.

Figure 3:
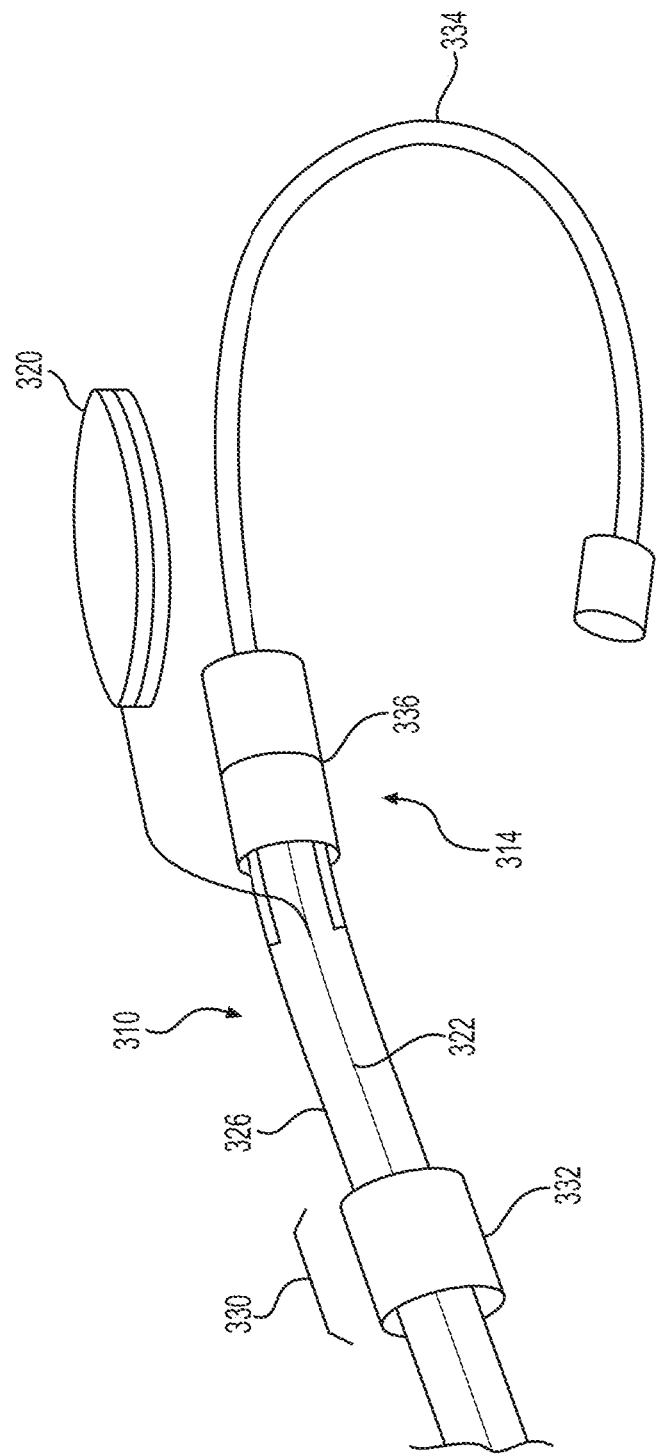
FIG. 3 is an embodiment of the device, particularly showing the anchor portion 330 and a proximal portion ending at the open proximal end 314 of the catheter 310 of the device, the main control unit 320 of the device, and the extension set 334.

The main control unit 320 is disposed external to the subject and connected to the sensors 318 via the wire 322. In one embodiment, a portion of the wire 322 is disposed between the outer wall 326 and the inner wall 324 of the catheter 310 such that this portion of the wire 322 associated with the catheter 310 is not able to contact the peritoneal fluid in the central lumen 316 or be exposed to the environment outside the catheter 310, with an additional portion of the wire 322 extended from the portion associated with the catheter 310 to connect with the main control unit 320 as shown in FIG. 3. In another embodiment, the wire 322 may be entirely or substantially entirely (e.g. 80-100%, or 85-95% of the total length of the wire) disposed between the outer wall 326 and the inner wall 324 of the catheter 310, with no or a very short extended portion connected to the main control unit 320, such that the main control unit 320 is integrated or substantially integrated with the catheter 310. In one embodiment, a portion or substantially the entirety of the wire 322 is embedded between the outer wall 326 and the inner wall 324 of the catheter 310. In another embodiment, there may be a space between the inner wall 324 and outer wall 326 defining a minor lumen along the length of the catheter 310, and a portion or substantially the entirety of the wire 322 may be placed inside the minor lumen. Unlike the central lumen 316, the minor lumen is configured so as to not allow entry of the peritoneal fluid into the minor lumen and exposure of the wire 322 to the peritoneal fluid. This is an advantageous embodiment for easy replacement of the wire 322, since when the wire 322 is disconnected from the main control unit 320 and the sensors 318, the wire 322 can be conveniently removed from the minor lumen and a replacement wire can be inserted into the minor lumen and subsequently connected with the main control unit 320 and the sensors 318. The wire 322 may be connected to the sensors 318 at a location between the outer wall 326 and the inner wall 324 of the catheter 310. For example, an end of the wire 322 may be connected to an end of a microelectrode of an electrochemical sensor, with both the end of the wire and the end of the microelectrode disposed or embedded between the outer wall 326 and the inner wall 324 of the catheter 310. Alternatively, an end of the wire 322 connected to the sensors 318 may be extended from between the outer wall 326 and the inner wall 324 to the surface of the inner wall 324 to link with the sensors 318. However, the extended portion of the wire 322 must be properly insulated from the peritoneal fluid, for example, with a plastic or rubber-like polymer insulator sheath.

In one embodiment, the main control unit 320 is attached to the catheter 310 via the wire 322 at or near the open proximal end 314. In another embodiment, the main control unit 320 is attached to the catheter 310 via the wire 322 at any location as long as the main control unit 320 is disposed external to the subject.

In some embodiments, the one or more sensors 318 of the device are configured to detect and quantify the concentration of at least one analyte selected from the group consisting of glucose, hydrogen ion (for determining pH), urea, and creatinine in real time, preferably regularly, preferably frequently, more preferably continuously. The sensors 318 are preferably electrochemical sensors with one or more microelectrodes for each sensor. For example, the microelectrodes may be components of a two electrode system comprising a working electrode and a reference electrode, or may be components of a three electrode system comprising a working electrode, a reference electrode, and a counter electrode. In some embodiments, the electrochemical sensors use amperometric detection and/or potentiometric detection techniques and are powered and controlled by the main control unit 320 via the wire 322. For example, in response to input from the patient, health care provider or other operators, the main control unit 320 can activate (power on) or deactivate (power off) the sensors, change the operating potential on the microelectrodes of the sensors and/or the operating current passing through the microelectrodes of the sensors, and specify operational modes for the sensors 318, e.g. regular or continuous detection and quantification of the analytes.

Suitable glucose sensors may include, without limitation, glucose oxidase (GOx)-based amperometric biosensors of glucose using either oxygen or a non-physiological (synthetic) electron acceptor, preferably configured for continuous in vivo glucose monitoring, e.g. implantable needle glucose biosensors manufactured by Medtronic Inc and Abbott Inc (See Joseph Wang, Electrochemical Glucose Biosensors, Chem. Rev. 2008, 108, 814-825, incorporated herein by reference in its entirety), and a glucose sensor for the continuous glucose monitoring system by Dexcom, where the glucose sensor comprises a platinum working electrode configured to react electrochemically with a fluid containing glucose to oxidize glucose proportionally to its concentration (See U.S. Pat. No. 8,926,585 B2, incorporated herein by reference in its entirety).

A suitable urea biosensor may be a single-walled carbon nanotube-based micron scale multiplex biosensor configured to detect urea (as well as glucose) as disclosed in International Application Publication No. WO2015021063 A1, incorporated herein by reference in its entirety.

Suitable pH biosensors may be an in vivo electrochemical hydrogen ion sensor disclosed in U.S. Pat. No. 3,911,901 A, incorporated herein by reference in its entirety, and an in vivo electrochemical pH sensor disclosed in U.S. Pat. No. 6,694,161 B2, incorporated herein by reference in its entirety.

An exemplary suitable creatinine in vivo sensor may be an in vivo creatinine sensor disclosed in U.S. Pat. No. 5,520,178 A, incorporated herein by reference in its entirety.

The one or more sensors 318 described above communicate with the main control unit 320 via the wire 322. In one embodiment, the main control unit 320 is configured to provide electrical power, e.g. from a battery, to the sensors 318, to receive the detection and quantification signals or data for the analytes from the sensors 318, store the data, e.g. in a memory, and to transmit the data to a second device, such as a computer, a smart phone (e.g. an Android based smart phone, a Windows based smart phone, and an Apple iOS based iPhone), a smart watch (e.g. an Apple watch, and a Samsung Gear S watch), a cloud computer server, and a pager, preferably in real time, more preferably regularly in real time, more preferably frequently in real time, more preferably continuously in real time. The main control unit 320 may transmit the data to the second device over a wireless or wired link, or a combination thereof. The wireless link can be, without limitation, a Bluetooth link, an infrared link, a Wi-Fi link, and long-distance wireless technologies, e.g. a satellite link. The wired link can be, without limitation, USB cables and Ethernet.

Figure 5:
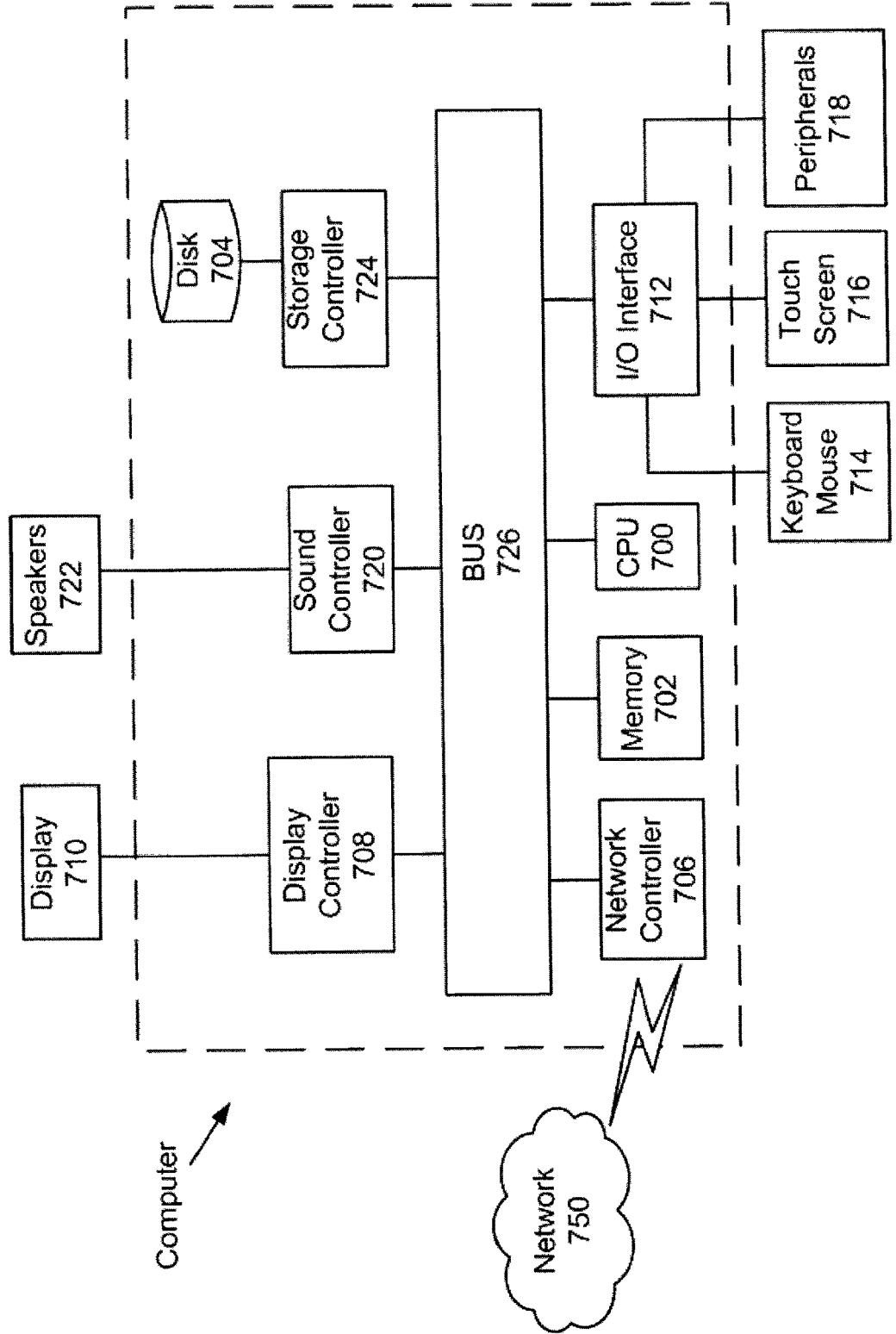
FIG. 5 is a graphical presentation of an embodiment of a computer configured as the second device.

In one embodiment, the second device is a computer illustrated in FIG. 5. In FIG. 5, the computer includes a CPU 700 which performs, for example, the analysis of the detection and quantification data from the sensors, generates and/or transmits an alert when the data vary from a pre-set (reference or baseline) value described below. The process data and instructions may be stored in memory 702. These processes and instructions may also be stored on a storage medium disk 704 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computer communicates, such as a server or computer.

Further, the claimed advancements may be provided as a utility application, background daemon, or component of an operating system, or combination thereof, executing in conjunction with CPU 700 and an operating system such as Microsoft Windows 7, UNIX, Solaris, LINUX, Apple MAC-OS and other systems known to those skilled in the art.

The hardware elements in order to obtain the computer may be realized by various circuitry elements, known to those skilled in the art. For example, CPU 700 may be a Xenon or Core processor from Intel of America or an Opteron processor from AMD of America, or may be other processor types that would be recognized by one of ordinary skill in the art. Alternatively, the CPU 700 may be implemented on an FPGA, ASIC, PLD or using discrete logic circuits, as one of ordinary skill in the art would recognize. Further, CPU 700 may be implemented as multiple processors cooperatively working in parallel to perform the instructions for the data analysis and alert generation and transmission.

The computer in FIG. 5 also includes a network controller 706, such as an Intel Ethernet PRO network interface card from Intel Corporation of America, for interfacing with network 750. As can be appreciated, the network 750 can be a public network, such as the Internet, or a private network such as an LAN or WAN network, or any combination thereof and can also include PSTN or ISDN sub-networks. The network 750 can also be wired, such as an Ethernet network, or can be wireless such as a cellular network including EDGE, 3G and 4G wireless cellular systems. The wireless network can also be WiFi, Bluetooth, or any other wireless form of communication that is known.

The computer further includes a display controller 708, such as a NVIDIA GeForce GTX or Quadro graphics adaptor from NVIDIA Corporation of America for interfacing with display 710, such as a Hewlett Packard HPL2445w LCD monitor. A general purpose I/O interface 712 interfaces with a keyboard and/or mouse 714 as well as a touch screen panel 716 on or separate from display 710. General purpose I/O interface also connects to a variety of peripherals 718 including printers and scanners, such as an OfficeJet or DeskJet from Hewlett Packard.

A sound controller 720 is also provided in the computer, such as Sound Blaster X-Fi Titanium from Creative, to interface with speakers/microphone 722 thereby providing sounds and/or music.

The general purpose storage controller 724 connects the storage medium disk 704 with communication bus 726, which may be an ISA, EISA, VESA, PCI, or similar, for interconnecting all of the components of the computer. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

In a preferred embodiment, the main control unit 320 comprises a microprocessor to process, analyze, and/or mathematically manipulate the data from the sensors 318, and generate and/or transmit an alert, for example, when the data indicate a deviation from a pre-set value or otherwise an abnormal condition of the peritoneal fluid, e.g. the acidity of the peritoneal fluid is above an acceptable level, and/or the glucose concentration of the peritoneal fluid is below an effective level to drive the filtration process by osmosis.

In another embodiment, the main control unit 320 may further comprise a display or monitor to display the data, preferably in real time. The display may be a liquid crystal display, a light emitting diode display, or a touch screen display. In a preferred embodiment, the second device comprises a display, such as an LCD or LED, and a touch screen display to display the data and/or alerts transmitted from the main control unit 320, a microprocessor for analysis or further analysis of the data and/or alerts transmitted from the main control unit 320 regarding the concentrations of the analytes in the peritoneal fluid and other information, e.g. battery levels and/or other aspects of the operational status of the main control unit 320 and the sensors 318, for outputting the data, the data analysis, and the other information via a display, a printer, and/or a USB drive and/or a DVD/CD-ROM to export a data file to a computer readable medium (e.g. a hard disk, a flash drive, a CD, and a DVD), and for generating and/or transmitting an alert, for example, when the data indicate a deviation from a pre-set value or otherwise an abnormal condition of the peritoneal fluid, e.g. the acidity of the peritoneal fluid is above an acceptable level, and/or the glucose concentration of the peritoneal fluid is below an effective level to drive the filtration process by osmosis. Such a microprocessor resident in the second device can advantageously provide some or all of the functionality of the microprocessor of the main control unit 320, thereby reducing the microprocessor requirements of the main control unit 320. In another preferred embodiment, the microprocessor resident in the second device controls the main control unit 320 such that a user of the second device may, for example, turn on or off the main control unit 320, and access the control functions of the main control unit 320 to activate or deactivate the sensors 318, change the operating potential on the microelectrodes of the sensors 318 and/or the operating current passing through the microelectrodes of the sensors 318, and select the operational modes of the sensors 318, e.g. regular or continuous detection and quantification of the analytes. The second device preferably has a keyboard for accepting input from a patient, a health care provider, or other operators of the device to, for example, activate the device, enter codes for establishing a wireless link between the main control unit 320 and the second device, and specify operational modes of the sensors 318, etc.

In a preferred embodiment, the sensors 318 of the device are configured to be able to detect and quantify the concentrations of the analytes regularly, frequently, or continuously and in real time. In another preferred embodiment, to take advantage of the regular, frequent, or continuous and real time detection and quantification capability of the sensors 318, the main control unit 320 and/or the second device are configured to be able to process, analyze and mathematically manipulate and output (e.g. by displaying and/or printing) the detection and quantification data from the sensors 318, preferably also in real time, and more preferably in a regular/frequent/continuous real time fashion.

In a preferred embodiment, the main control unit 320 and/or the second device are configured to generate and/or transmit an alert if the data from the sensors 318, e.g. the concentration of an analyte and the pH of the peritoneal fluid, vary from a baseline. The above can be achieved by equipping the main control unit 320 and/or second device with suitable microprocessors and computer software. The alert can be, for example, in the form of a visible and/or audible signal to the patient, health care worker, or other operators of the device. In one embodiment, the baseline is a baseline previously established from the subject. In another embodiment, the baseline is a value within a normal range of an analyte, or an average of the baseline values of an analyte from a group of subjects similar to the subject, e.g. a group of peritoneal dialysis patients, preferably matched by age, gender, and/or medical condition, etc.

In the course of the dwell, glucose diffuses from the dialysate to the blood and the glucose concentration in the peritoneal fluid becomes lower, making the osmotic ultrafiltration less effective. It will be advantageous to be able to regularly, frequently, or continuously monitor the glucose concentration in the peritoneal fluid in real time during the dwell with a glucose sensor of the device, so that a peritoneal dialysis patient or health care provider will know, or will be alerted by the main control unit and/or the second device, when the glucose concentration in peritoneal fluid falls below a certain level. The patient or the health care provider may then proceed to drain the peritoneal fluid and fill fresh peritoneal dialysis solution in the peritoneal cavity.

A peritoneal dialysis patient may experience pain or discomfort if the dialysate is too acidic. Additionally, a peritoneal dialysis patient with an end-stage kidney disease is prone to the malnutrition-inflammation-anemia (MIA) syndrome due to excess acid in the patient's body. It will be advantageous to be able to regularly, frequently, or continuously monitor the hydrogen ion concentration, or the pH, of the dialysate and/or the peritoneal fluid in real time in every step of the peritoneal dialysis procedure with a pH sensor of the device, so that a peritoneal dialysis patient or health care provider will know, or will be alerted by the main control unit and/or the second device and take corrective actions when the pH of the dialysate or the peritoneal fluid falls below a certain level.

When kidneys fail in a patient, waste products such as urea and creatinine build up in the blood. Peritoneal dialysis removes the waste products including urea and creatinine. Besides glucose at a high concentration, a typical peritoneal dialysis solution contains low concentrations of urea and creatinine such that urea and creatinine move from the blood to the peritoneal dialysis solution in the peritoneal cavity during the dwell. Urea and creatinine then leave the patient's body when the spent peritoneal dialysis solution is drained from the peritoneal cavity of the abdomen. The amount of fluid and solutes (e.g. urea and creatinine) moving from the blood to the peritoneal cavity depends on the rapidity with which glucose is absorbed and the ease with which the solutes move into the peritoneal cavity indicative of peritoneal membrane permeability. It will be advantageous to regularly, frequently, or continuously monitor the urea and creatinine concentrations in the peritoneal fluid in real time, particularly during the dwell, with the device equipped with a urea sensor and/or a creatinine sensor to help assess the peritoneal dialysis efficiency and the peritoneal membrane permeability in real time.

In a preferred embodiment, the main control unit 320 and/or the second device contain microprocessors and appropriate computer software instructions to process the real time detection and concentration quantification data of glucose, hydrogen ion, urea, and creatinine in various ways useful for evaluating the progress, status, and efficiency of peritoneal dialysis.

In one embodiment, the main control unit 320 and/or the second device are configured to determine and output by displaying, printing, and exporting a data file, for example, the real time concentrations of glucose, hydrogen ion, urea, and/or creatinine at any time point during the course of the peritoneal dialysis, either continuously or at desirable time intervals.

In another embodiment, the main control unit 320 and/or the second device are configured to determine, preferably in real time, a relationship of the concentration of the at least one analyte of glucose, hydrogen ion, urea, and creatinine with time based on the data received from the at least one sensor 318. The relationship is represented by a curve indicative of the concentration at each time (point), and the main control unit 320 and/or the second unit are configured to calculate, preferably in real time, an area under the curve between at least two selected time points. The size of the area under the curve for each analyte provides an aggregate result of the change in the concentration of each analyte with time either during the entire peritoneal dialysis process or a segment of the peritoneal dialysis process, depending on the time points selected for the calculation of the area under the curve, and may be compared with a pre-set value, e.g. a reference or baseline area under the curve, for evaluation. In a preferred embodiment, the main control unit 320 and/or the second device are configured to generate and/or transmit an alert if the area under the curve varies from a pre-set value or a reference/baseline value.

In still another embodiment, the main control unit 320 and/or the second device are configured to determine, preferably in real time, a relationship of the concentration of the at least one analyte of glucose, hydrogen ion, urea, and creatinine with time based on the data received from the at least one sensor 318 and calculate, preferably in real time, a rate of change in the concentration of the at least one analyte of glucose, hydrogen ion, urea, and creatinine at each time (point) and/or over a period of time based on the relationship. The results may be valuable in providing useful and actionable information on the instant or time averaged dynamic changes in the concentrations of the analytes taking place in the peritoneal fluid in real time. Specifically, the rate of change in glucose concentration is useful for assessing how rapidly glucose is absorbed, particularly during the dwell time of the peritoneal analysis. The rate of change in urea and/or creatinine concentration is useful for assessing how efficiently the subject's blood is filtered by the peritoneal dialysis at any time point or any given time period during the dwell time of the peritoneal dialysis. When a fresh peritoneal dialysis solution is first placed in the peritoneal cavity of the abdomen, it draws in wastes (e.g. urea and creatinine) rapidly. As wastes fill the peritoneal dialysis solution, the peritoneal dialysis solution cleans the blood less efficiently, i.e. it removes urea or creatinine from the blood less rapidly. The rates of changes in the concentrations of urea and creatinine across the timeline of peritoneal dialysis help determine the number of daily exchanges and the dwell time to achieve an efficient peritoneal dialysis. The rate of change in the hydrogen ion concentration obtained in real time may advantageously help health care providers foresee any acidification in the peritoneal fluid and take timely preventive or corrective actions. In some embodiments, the main control unit 320 and/or the second device are configured to generate and/or transmit an alert if the rate of change varies from a pre-set value.

In one embodiment, there may be more than one wire, or a bundle of wires connecting the main control unit 320 with the sensors 318, since the sensors 318 described above are preferably electrochemical sensors comprising one or more microelectrodes for each sensor and each microelectrode may be connected to the main control unit 320 via a separate wire. In a preferred embodiment, the material for the wire or the bundle of wires is a non-magnetic conductive material that is MRI-safe. Non-limiting examples of the suitable non-magnetic conductive material include non-magnetic metallic conductors (e.g. aluminum, copper, zinc, titanium, gold, silver, and platinum), non-metallic conductors, such as graphite and conductive polymers (e.g. polyfluorenes, polyphenylenes, polypyrenes, polyazulenes, polynaphthalenes, polypyrroles, polycarbazoles, polyindoles, polyazepines, polyanilines, polythiophenes, poly(3,4-ethylenedioxythiophene), poly(p-phenylene sulfide), polyacetylenes, and polyphenylene vinylene, combinations of different non-magnetic metallic conductors or different non-metallic conductors, and combinations of at least one non-magnetic metallic conductor and at least one non-metallic conductor.

Figure 4:
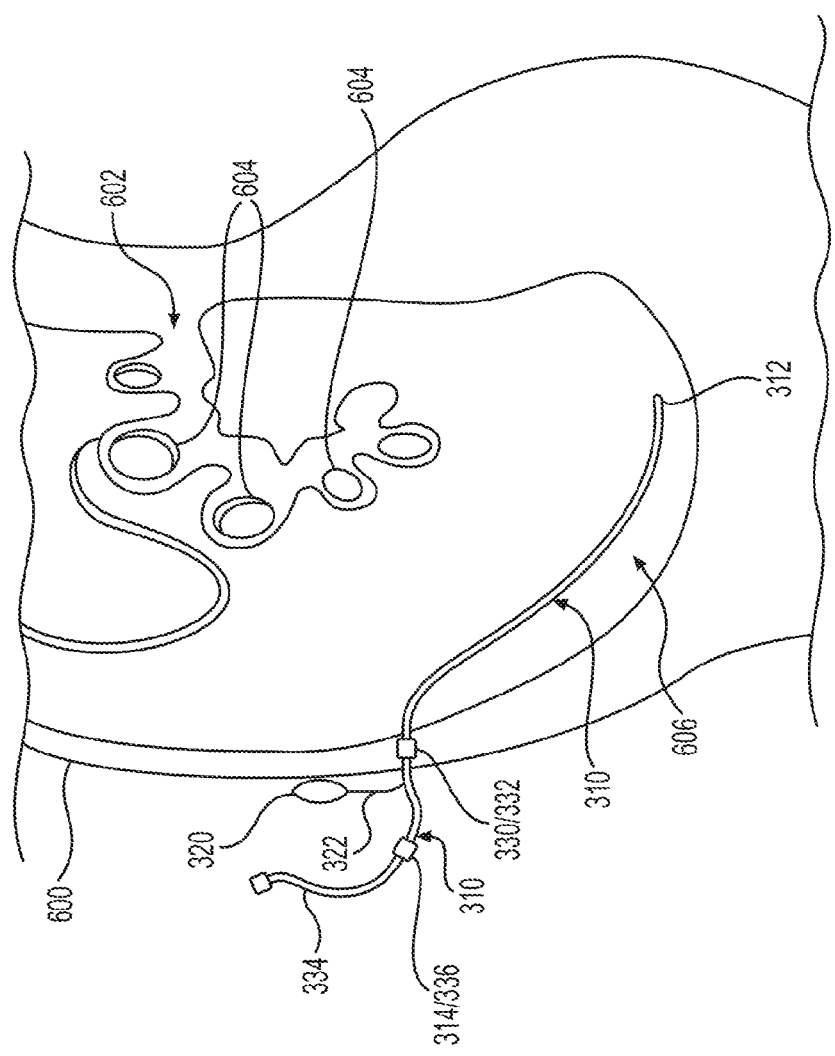
FIG. 4 shows an embodiment of the device when placed on a patient undergoing peritoneal dialysis treatment.

Referring to FIG. 3, in one embodiment, the device further comprises an extension set 334 connected to the open proximal end 314 of the catheter 310 at the connection point 336. The extension set 334 may be connected to a bag containing a fresh peritoneal dialysis solution during filling or refilling of a peritoneal dialysis procedure, or connected to a disposal bag or container for disposing of a spent peritoneal dialysis solution during draining of a peritoneal dialysis procedure. FIG. 4 shows the device with the extension set when it is used on a peritoneal dialysis patient. When the device is in use, the open distal end 312 of the catheter 310 is inserted into the peritoneal cavity 606 of the patient. The open proximal end 314 of the catheter 310 is disposed external to the patient and connected to the extension set 334 at the connection point 336. The distal portion of catheter disposed within the peritoneal cavity 606 is the intra-peritoneal segment (shown by the lower arrow from 310) of the catheter 310. The anatomical locations of bowel loops and mesentery are represented by 604 and 602, respectively. The anchor portion 330 of the catheter 310 is anchored in the abdominal wall 600 by a Dacron cuff 332 surrounding the outer wall of the anchor portion 330. The main control unit 320 is located external to the patient and adjacent to the open proximal end 314 and is attached to the catheter 310 via an extension of the wire 322, a portion of which is embedded between the outer wall and the inner wall of the catheter 310 and connecting the main control unit 320 with the sensors (not shown) at or adjacent to the open distal end 312 of the catheter 310.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present disclosure is intended to cover alternatives, modifications, and equivalents, which may be included within the spirit and scope of the present inventions as defined by the claims.

The invention claimed is:

1. A device for in vivo detecting and quantifying a concentration of at least one analyte in a peritoneal fluid of a subject, the device comprising:
   (a) a catheter configured for insertion through an abdominal wall into a peritoneal cavity comprising the peritoneal fluid of the subject,
   wherein the catheter comprises an elongated tube having an open proximal end, an open distal end, an anchor portion disposed between the open proximal end and the open distal end, an outer wall, and an inner wall disposed within the outer wall and defining a central lumen for conveying the peritoneal fluid,
   wherein the open proximal end is configured to be disposed external to the subject, the open distal end is configured to be disposed within the peritoneal cavity of the subject, and the anchor portion is configured to be disposed within and anchored to the abdominal wall,
   (b) at least one sensor disposed on a surface of the inner wall of the catheter at or adjacent to the open distal end,
   wherein the at least one sensor is configured to contact the peritoneal fluid and to detect and quantify the concentration of at least one analyte in the peritoneal fluid in real time, wherein the at least one analyte is selected from the group consisting of glucose, hydrogen ion, urea, and creatinine, and
   (c) a processing circuitry disposed external to the subject and connected to the at least one sensor via at least one wire, wherein at least a portion of the at least one wire is disposed between the inner wall and the outer wall of the catheter,
   wherein the processing circuitry is configured to control the at least one sensor, to receive and store data of the detection and quantification of the at least one analyte in the peritoneal fluid from the at least one sensor via the at least one wire, and to transmit the data to a second device having a second processing circuitry,
   wherein the processing circuitry and/or the second processing circuitry of the second device are configured to determine a relationship of the concentration of the at least one analyte of glucose, hydrogen ion, urea, and creatinine with time based on the data received from the at least one sensor,
   wherein the relationship is represented by a curve indicative of the concentration at each time,
   wherein the processing circuitry and/or the second processing circuitry of the second device are configured to calculate an area under the curve indicative of the concentration at each time,
   wherein the processing circuitry and/or the second processing circuitry of the second device are further configured to generate and/or transmit an alert if the area under the curve varies from a pre-set value.

2. The device of claim 1, wherein the catheter further comprises a plurality of openings disposed on a distal portion of the catheter, wherein the plurality of openings pass through the outer wall and the inner wall without the at least one wire therebetween, and wherein the distal portion of the catheter is configured to contact the peritoneal fluid.

3. The device of claim 1, further comprising a display for displaying the data.

4. The device of claim 1, wherein the processing circuitry is further configured to analyze the data.

5. The device of claim 1, wherein the processing circuitry is configured to transmit the data to the second device via a wired link, a wireless link, or a combination thereof.

6. The device of claim 5, wherein the wireless link is at least one selected from the group consisting of a Bluetooth link, an infrared link, a Wi-Fi link, and a satellite link.

7. The device of claim 1, wherein the second device is at least one selected from the group consisting of a computer, a smart phone, a smart watch, a pager, and a cloud computer server.

8. The device of claim 1, wherein the second processing circuitry of the second device is configured to analyze the data.

9. The device of claim 1, wherein the subject is a human or an animal.

10. The device of claim 1, wherein the at least one wire is made of a non-magnetic conductive material.

11. The device of claim 10, wherein the non-magnetic conductive material is at least one selected from the group consisting of aluminum, copper, zinc, titanium, gold, silver, platinum, graphite, a polyfluorene, a polyphenylene, a polypyrene, a polyazulene, a polynaphthalene, a polypyrrole, a polycarbazole, a polyindole, a polyazepine, a polyaniline, a polythiophene, poly(3,4-ethylenedioxythiophene), poly(p-phenylene sulfide), a polyacetylene, and polyphenylene vinylene.

12. The device of claim 1, wherein a Dacron cuff is disposed on the outer wall of the anchor portion for anchoring the catheter in the abdominal wall.

13. The device of claim 1, further comprising an extension set connected to the open proximal end of the catheter.

14. The device of claim 1, wherein the processing circuitry and/or the second processing circuitry of the second device are configured to generate and/or transmit an alert if the data vary from a baseline.

15. The device of claim 14, wherein the baseline is a baseline previously established from the subject.

16. The device of claim 1, wherein the processing circuitry and/or the second processing circuitry of the second device are configured to determine a relationship of the concentration of the at least one analyte of glucose, hydrogen ion, urea, and creatinine with time based on the data received from the at least one sensor and calculate a rate of change in the concentration of the at least one analyte of glucose, hydrogen ion, urea, and creatinine at each time and/or over a period of time based on the relationship.

17. The device of claim 16, wherein the processing circuitry and/or the second processing circuitry of the second device are further configured to generate and/or transmit an alert if the rate of change varies from a pre-set value.

* * * * *